United States Patent
Chinn

[11] Patent Number: 5,976,092
[45] Date of Patent: Nov. 2, 1999

[54] COMBINATION STEREOTACTIC SURGICAL GUIDE AND ULTRASONIC PROBE

[76] Inventor: Douglas O. Chinn, 1366 N. Santa Anita Ave., Arcadia, Calif. 91006

[21] Appl. No.: 09/097,400

[22] Filed: Jun. 15, 1998

[51] Int. Cl.[6] .................................................. A61B 8/00
[52] U.S. Cl. ............................................................. 600/459
[58] Field of Search .................................. 600/459, 461, 600/462, 467

[56] References Cited

U.S. PATENT DOCUMENTS

| | | | |
|---|---|---|---|
| 5,178,148 | 1/1993 | Lacoste et al. | 600/462 |
| 5,398,690 | 3/1995 | Batten et al. | 600/461 |

*Primary Examiner*—Scott M. Getzow
*Assistant Examiner*—Maulin Patel
*Attorney, Agent, or Firm*—Morland C. Fischer

[57] ABSTRACT

A stereotactic surgical guide to be coupled to the shaft of a conventional ultrasonic probe for use during cryosurgery to enable a surgeon to easily, efficiently and accurately position one or more cryosurgical probes in the body of the patient for producing iceballs to kill cancer cells at a localized tissue area. The stereotactic surgical guide includes a laser carrying plate that carries a laser and is coupled to a worm drive. The distance between the ultrasonic probe and the organ in need of treatment is visually determined on the monitor of an ultrasound machine, and the worm drive is rotated to cause the laser carrying plate to move a corresponding distance, whereby the laser will be positioned in spaced opposing alignment with the organ. The laser is then energized and a light beam aimed towards the patient's body to establish a target through which the cryosurgical probe will be inserted to penetrate the body.

10 Claims, 3 Drawing Sheets

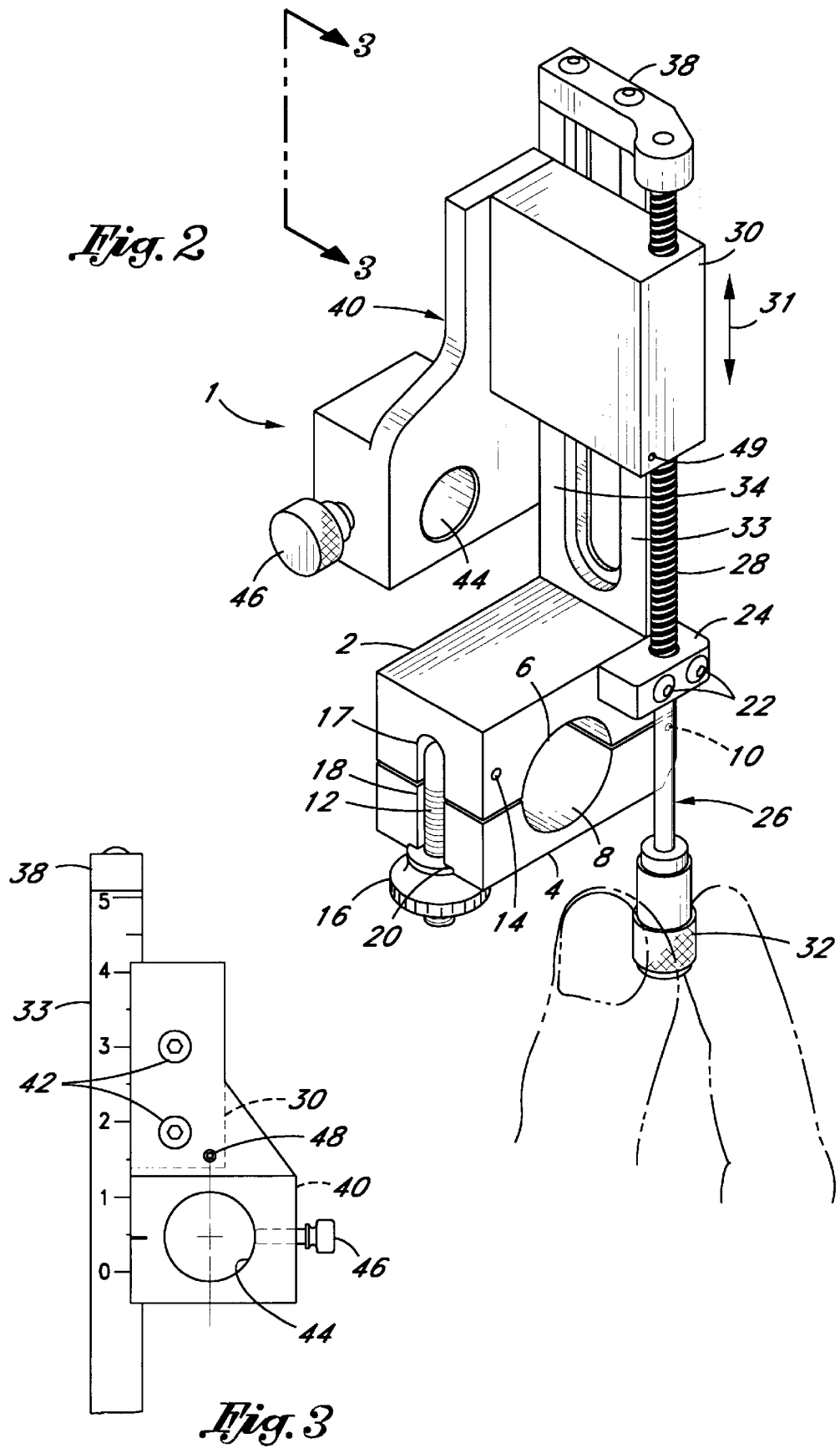

COMBINATION STEREOTACTIC SURGICAL GUIDE AND ULTRASONIC PROBE

BACKGROUND OF INVENTION

1. Field of the Invention

This invention relates to a stereotactic surgical guide to be detachably coupled to a conventional ultrasonic probe for use during cryosurgery to provide a laser generated aiming beam and thereby enable the accurate placement of a cryosurgical probe for producing iceballs at a localized tissue area within the body of a patient undergoing treatment for cancer.

2. Background Art

Techniques are known by which to cryosurgically destroy cancer cells in the tissue of a patient undergoing treatment. In general, a liquid or gas cryogen is used to generate extremely low temperatures sufficient to kill malignant cells. In some cases, a cryosurgical probe penetrates the patient's tissue (e.g. the prostate, liver, breast and brain) to deliver the cryogen and thereby form an iceball adjacent to the organ to be treated.

However, the size and shape of human organs vary from one patient to the next. Therefore, a significant problem faced by surgeons who practice cryosurgery is the accurate location of the iceball within the body of the patient. For example, should an iceball be misplaced relative to a patient's prostate, there is the risk that the neighboring sphincter will become frozen leading to the possibility of incontinence. Moreover, there may be an incomplete freezing of the cancerous cells in the prostate gland or an undesirable freezing beyond the prostate and into the bladder or rectum which could cause a urethral-fistula.

Guides have been used to position a cryosurgical probe within the body of a patient. However, the conventional guides have proven to cumbersome and are known to block or impede the easy insertion of the probe. In cases where the cryosurgical probe must be flared (i.e. angled) upon entering the patient's body, access to the skin surface adjacent the point of penetration is sometimes not readily available such that a special proven design is required. As a consequence of the foregoing, the ability of the surgeon to accurately position the cryoprobe is reduced while the cost and inconvenience associated with conventional guides are increased.

Therefore, what is needed is a surgical guide by which to enable surgeons to easily, efficiently and accurately insert and position a cryosurgical probe and/or a suitable positioning needle depending upon the location, size and type of tissue to be treated so as to confine the cryogenic effect to a localized cancerous area and thereby avoid the risks and inconvenience that are associated with conventional guides and techniques.

SUMMARY OF THE INVENTION

This invention relates to a stereotactic surgical guide for use with a conventional ultrasonic probe during cryosurgery to enable a surgeon to easily, efficiently and accurately place one or more cryosurgical probes and/or Onik positioning needles in the body of the patient for producing iceballs that are sized and strategically located to kill cancer cells. The stereotactic guide includes upper and lower clamshell gripping members that are rotated towards one another so as to surround the shaft of the ultrasonic probe and thereby detachable clamp the guide to the probe. A rotatable worm drive having a threaded portion is coupled to a block support so that a rotation of the worm drive causes an up or down movement of the block support. The guide also has a pair of guide rails along which the block support will slide to ensure a smooth movement of the block support in response to a rotation of the worm drive. Attached to and movable with the block support is a laser carrying plate. A hole extends through the laser carrying plate in which to receive and retain a helium-neon laser. The laser and the ultrasonic probe are retained so as to lie in spaced parallel alignment one above the other.

In operation, the ultrasonic probe is inserted in a body cavity of the patient. By watching the monitor of an ultrasound machine, the surgeon visually determines the distance between the ultrasonic probe and the intended location of the cryosurgical probe that will be necessary to deliver a cryogen to the cancerous tissue so as to produce an iceball sufficient for killing the cancer cells. The surgeon then rotates the worm drive which causes a movement of the block support and the laser carrying plate attached thereto. Accordingly, the laser is simultaneously moved relative to the ultrasonic probe by a distance that corresponds to the distance between the ultrasonic probe and the intended location of the cryosurgical probe, whereby the laser is now positioned to lie in spaced axial alignment with the tissue area in need of treatment. The laser is then activated and a light beam is aimed towards the patient's skin to establish a target thereagainst through which the cryosurgical probe and/or positioning needle will be inserted to penetrate the patient's body. The stereotactic surgical guide is now removed from the ultrasonic probe and the probe is used as usual to monitor the angle and depth of the cryosurgical probe so as to achieve a reliable cryogenic effect.

BRIEF DESCRIPTION OF THE DRAWINGS

FIG. 2 illustrates the details of the stereotactic surgical guide of FIG. 1 removed from the ultrasonic probe;

FIG. 3 is a partial rear elevational view of the stereotactic guide;

DETAILED DESCRIPTION

Figure 1:
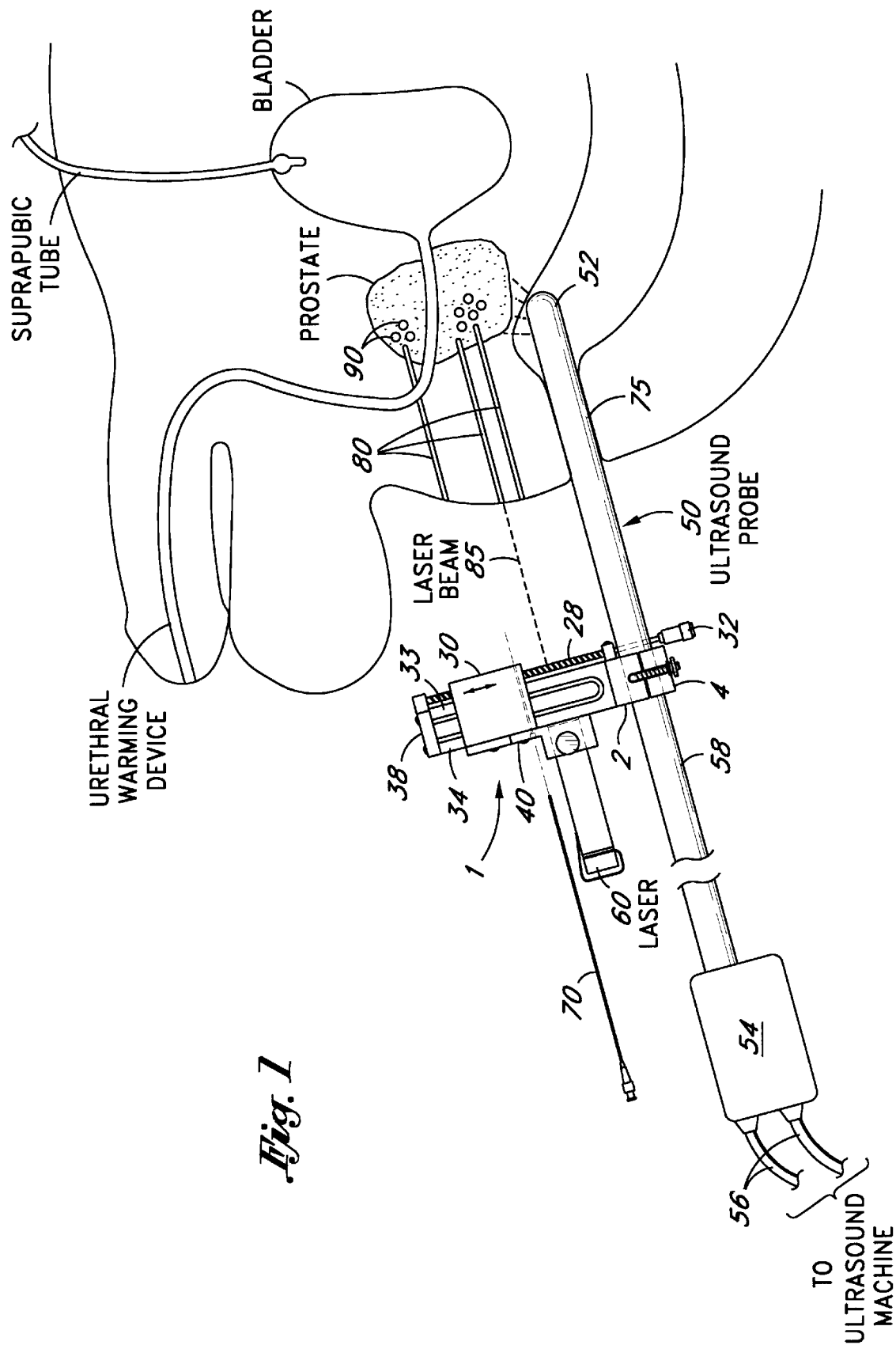
FIG. 1 shows the stereotactic surgical guide of this invention coupled to a conventional ultrasonic probe with the probe inserted in the rectum of a patient undergoing treatment for cancer.

The stereotactic surgical guide 1 of this invention will be best understood by first describing the ultrasonic probe shown in FIG. 1 of the drawings to which the stereotactic guide is coupled. The ultrasonic probe 50 is a commercially available device that is commonly used during surgical procedures to provide an image of an organ of a patient in need of treatment (e.g. for cancer). The probe 50 has a nose 52 one at end to surround and protect a biplanar transrectal ultrasound transducer (not shown). Located at the opposite end is a handle 54 at which the ultrasonic probe 50 is grasped and manipulated relative to the patient's body. A pair of cables 56 extends from the transducer within the nose 52 and outwardly of the handle 54 for connection to an ultrasound machine that is adapted to produce an image at an adjacent video monitor.

Located between the nose 52 and handle 54 of ultrasonic probe 50 is an elongated shaft 58 that is suitable to permit the probe to be placed deep within a body cavity of the patient. To this end, the shaft 58 typically has a series of equally spaced positioning lines to enable the surgeon to accurately measure the depth of the nose 52 and the transducer surrounded thereby. The ultrasonic probe 50 described above and illustrated in FIG. 1 is conventional and, therefore, its operation will not be described. In this regard, and by way of example, the ultrasonic probe 50 to which the stereotactic surgical guide 1 is coupled is manufactured by Aloka Corporation.

Figure 4:
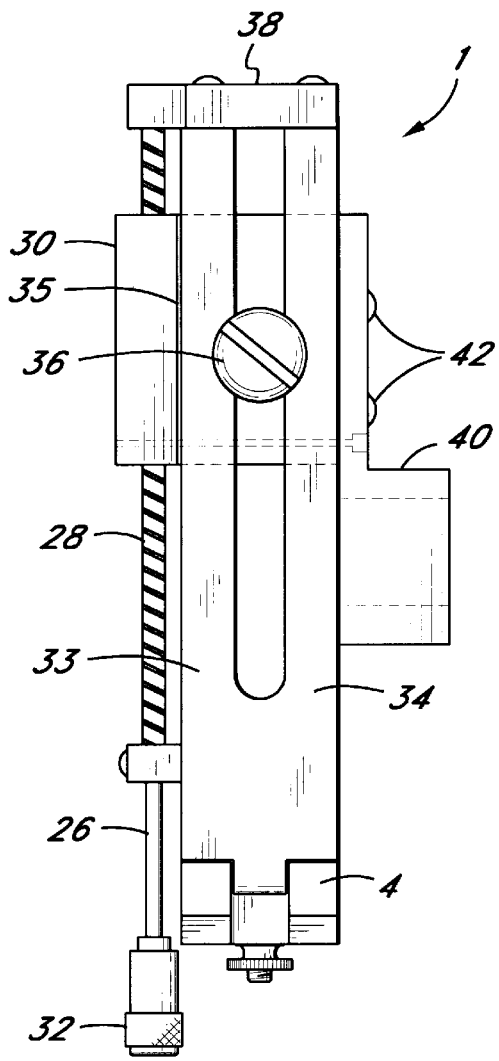
FIG. 4 is a side view of the stereotactic surgical guide.

The details of the stereotactic surgical guide 1 are now disclosed while now referring concurrently to FIGS. 2–4 of the drawings. Stereotactic guide 1 includes a clamshell grip including a pair of upper and lower gripping halves 2 and 4. Each of the pair of gripping halves 2 and 4 has an opposing arcuate cavity 6 and 8 formed therein (best shown in FIG. 2). The lower gripping half 4 is pivotally connected to the upper gripping half 2 by means of pivot pin 10. As shown in FIG. 1, with the lower gripping half 4 rotated towards and closed against the upper gripping half 2, the clamshell grip is closed around and detachably coupled to the shaft 58 of the ultrasonic probe 50. In particular, the shaft 58 is received within the opposing arcuate cavities 6 and 8 of the upper and lower gripping halves 2 and 4 to prevent an inadvertent removal or displacement of the probe 50 relative to the guide 1.

A latch is provided to retain the upper and lower gripping halves 2 and 4 closed against one another and clamped in surrounding engagement with the shaft 58 of ultrasonic probe 50. The latch includes a screw threaded rod 12, one end of which is pivotally connected to the upper gripping half 2 by means of a pivot pin 14. A lock nut 16 having a hollow threaded interior is attached to the opposite end of the threaded rod 12. The threaded lock nut 16 is adapted to ride along the threaded rod 12 in response to a rotation of the nut 16. With the clamshell grip closed around the ultrasonic probe 50, the threaded rod 12 is rotated around pivot pin 14 into a groove formed by end-to-end channels 17 and 18 running through each of the upper and lower gripping halves 2 and 4. The lock nut 16 is then rotated in a clockwise direction so as to move along the rod 12 towards the lower gripping half 4 until the threaded nut 16 is seated within a slot 20 formed in the bottom of gripping half 4. In other words, a portion of lock nut 16 will be tightened down against and countersunk within the slot 20 in lower gripping half 4 to securely hold the pair of gripping halves 2 and 4 in the closed position, one above the other, with the shaft 58 of probe 50 captured therebetween and retained in the respective arcuate cavities 6 and 8 thereof. In this same regard, lock nut 16 can be loosened within slot 20 to enable the guide 1 to be adjusted on probe 50 without opening the upper and lower gripping halves 2 and 4 which could otherwise cause a disengagement of guide 1 from probe 50.

When it is desirable to remove the stereotactic surgical guide 1 from the ultrasonic probe 50, the lock nut 16 is rotated in a counterclockwise direction around threaded rod 12 so as to be unseated from the slot 20 and moved away the lower gripping half 4 of the clamshell grip that surrounds the probe shaft 58. The rod 12 is then rotated outwardly from the channels 17 and 18 in gripping halves 2 and 4, whereby to now permit the lower gripping half 4 to rotate around pivot pin 10 and away from the upper gripping half 2. With the lower and upper gripping halves 2 and 4 rotated apart from one another and the clamshell grip moved to the opened position, the ultrasonic probe 50 will be free from its prior engagement with the clamshell grip.

Secured to the upper gripping half 2 by means of rivets 22, or the like, is a drive guide 24. The drive guide 24 is provided with an opening extending therethrough for receiving an elongated worm drive 26 having a threaded portion 28. A block support 30 has a longitudinally extending passageway in which to receive the threaded portion 28 of worm drive 26, whereby the block support 30 is coupled to worm drive 26 and adapted to ride up and down in the directions represented by reference arrows 31 along the threaded portion 28 in response to a rotation of the worm drive 26. To this end, a knurled knob 32 is affixed to one end of the worm drive 26 so as to impart a rotation to the threaded portion 28 and thereby cause the block support 30 to travel therealong.

To provide for the stable travel of the block support 30 along the threaded portion 28 of worm drive 26, the block support 30 is coupled to and adapted to slide against a pair of guide rails 33 and 34 that are disposed in parallel alignment with one another alongside the threaded portion 28. In this case, and is best shown in FIG. 4, the pair of guide rails 33 and 34 are disposed within a recess 35 formed in the back of block support 30. The guide rails 33 and 34 are spaced from one another, and a screw 36 projects through the space therebetween and into the support block 30 such that the head of the screw 36 is positioned against the backs of the rails 33 and 34. Therefore, the fronts of the rails 33 and 34 are positioned flush against the back of block support 30 to enable the block support and the screw 36 attached thereto to ride smoothly along the worm drive 26 while sliding upwardly or downwardly against the pair of guide rails 33 and 34 depending upon the direction in which the knurled knob 32 is rotated.

The pair of guide rails 33 and 34 are coextensively connected at first ends to the upper gripping half 2 of the clamshell grip that will hold the stereotactic surgical guide 1 in surrounding engagement with the ultrasonic probe 50. The opposite ends of the rails 33 and 34 are secured to a cover plate 38 by means of rivets, or the like. In this same regard, the threaded portion 28 of worm drive 26 located opposite the knurled knob 32 is also connected to the cover plate 38. The attachment of worm drive 26 and guide rails 33 and 34 to cover plate 38 maintains the parallel alignment of the drive 26 and rails 33 and 34 so as to contribute to the smooth travel of the block support 30 in order to accurately position a laser in a manner that will soon be disclosed.

Figure 5:
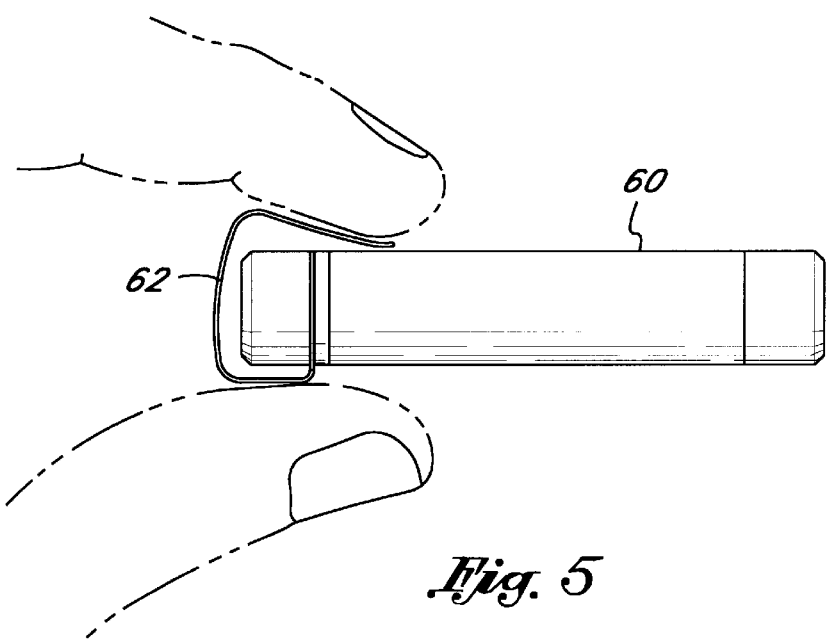
FIG. 5 illustrates a laser which is carried by the stereotactic surgical guide so that the position of the laser can be selectively adjusted for generating an aiming beam to establish a target against the patient's body at which to insert a cryosurgical probe.

A laser carrying plate 40 is secured to one side of the block support 30 by means of rivets 42, or the like. Therefore, the laser carrying plate 40 will move with block support 30 as it rides up and down along the threaded portion 28 of worm drive 26 when the knurled knob 32 is rotated. The laser carrying plate 40 has a (e.g. round) hole 44 extending longitudinally therethrough in which to receive a laser 60. Referring briefly to FIG. 5 of the drawings, the laser 60 is shown having a cylindrical body, although the shape of the laser is not to be regarded as a limitation of this invention.

By way of example, the laser 60 that is coupled to the laser carrying plate 40 at the hole 44 therein is a conventional low power helium-neon laser that is adapted to emit a beam of visible (e.g. red) light which provides a target spot by which a surgeon can accurately position a cryoprobe so as to achieve a desirable cryogenic effect that will be described in greater detail hereinafter. In this regard, the laser 60 has an on-off switch 62 at a manually accessible location, the closure of which causes the laser 60 to emit the beam of visible light to establish a target point on the skin of a patient undergoing treatment.

A threaded locking screw 46 projects laterally through the laser carrying plate 40 so as to intersect the longitudinally extending hole 44 and thereby engage the laser 60 located within the hole 44. By rotating and tightening the locking screw 46 against the laser 60, the laser will be retained within the hole 44 and thereby detachably connected to the laser carrying plate 40. Therefore, the laser 60 will be displaced along with laser carrying plate 40 as the laser carrying plate moves with the block support 30 to which plate 40 is secured in order to selectively position the laser 60 and correspondingly adjust the location of the light beam generated by the laser. To this end, a series of uniformly spaced referenced markings are printed on or etched into a side of the guide rail 33 that lies adjacent the laser carrying plate 40 (best in shown in FIG. 3). The reference markings enable the surgeon to precisely identify and track the position of the laser 60 as the laser carrying plate 40 moves with block support 30 in response to a rotation of the knurled knob 32 at one end of the worm drive 26.

A longitudinally extending needle guide hole 48 (best shown in FIG. 3) is formed through the laser carrying plate 40. It is important that the needle guide hole 48 through laser carrying plate 40 be located directly above the hole 44 through plate 40 such that the longitudinal axis of guide hole 48 lies in parallel alignment with the longitudinal axes of the hole 44 and the laser 60 to be located therewithin. As is best shown in FIG. 2, a needle port 49 extends laterally through the block support 30. The needle guide hole 48 through laser carrying plate 40 and the needle port 49 through block support 30 are axially aligned with one another so as to form a passageway to receive and support an alignment needle (designated 70 in FIG. 1) therethrough. Thus, it may be appreciated that the alignment needle 70 extending through needle guide hole 48 and needle port 49 will lie in parallel alignment with the laser 60 supported within the hole 44 through laser carrying plate 40.

With the stereotactic surgical guide 1 of this invention coupled to the ultrasonic probe 50 as described above, the guide 1 and probe 50 can be efficiently used to enable a surgeon to energize the aforementioned laser 60 so as to illuminate a target spot on the skin of the patient at which a cryosurgical probe and/or an Onik positioning needle or its equivalent will penetrate the body to reach an organ to be treated by cryosurgical techniques. The details concerning the use of stereotactic surgical guide 1 for this purpose are now disclosed while referring particularly to FIG. 1.

With the alignment needle 70 moved axially through the passageway formed by the needle guide hole 48 and the needle port 49 of the laser carrying plate 40 and the block support 30, the stereotactic surgical guide 1 is initially aligned with the ultrasonic probe 50. This alignment is performed before the surgical procedure and is typically completed in a bowl of water. The surgeon watches the monitor of the ultrasound machine to which the ultrasonic probe 50 is electrically connected at the same time that he rotates the stereotactic guide 1 around the probe 50. The stereotactic guide 1 is manipulated until the surgeon makes a visual determination on the monitor that the alignment needle 70 is positioned directly above and in the path of the energy beam generated by the transducer of the ultrasonic probe 50. Once the desired alignment has been obtained, the stereotactic guide 1 and the ultrasonic probe 50 are removed from the bowl of water, the guide 1 is clamped to the probe 50 in the manner described above, and the alignment needle 70 is withdrawn from the guide. Since the alignment needle 70 is initially held directly above and in parallel alignment with the laser 60, the laser 60 carried by the laser carrying plate 40 of guide 1 and the ultrasonic probe 50 will also be aligned, such that the longitudinal axes of the alignment needle 70, the laser 60 and the ultrasonic probe 50 will be arranged in spaced parallel alignment one above the other.

With the laser 60 and the ultrasonic probe 50 now aligned to one another and the alignment needle 70 removed from the stereotactic surgical guide 1, the probe 50 is inserted within a body cavity (e.g. the rectum 75 as shown in FIG. 1) of the patient undergoing treatment. In the alternative, it is to be understood that the ultrasonic probe 50 may be placed directly upon a body surface (e.g. the breast) or directly on an organ if a surgical incision has been made to open the patient. The surgeon then watches the monitor of the ultrasound machine to determine the location of the organ in need of treatment and the desired placement of one or more transperinel cryosurgical probes 80 and/or positioning needles.

More particularly, and depending upon the distance between the intended location of a cryosurgical probe 80 and the longitudinal axis of the ultrasonic probe 50 (which appears as a reference line on the monitor), the surgeon rotates the knurled knob 32 to rotate the threaded portion 28 of the worm drive. A rotation of the threaded portion 28 in turn causes the block support 30 and the laser carrying plate 40 of the stereotactic guide 1 to move up or down relative to the ultrasonic probe 50 by a distance (represented by the reference lines along the guide rail 33 shown in FIG. 3) corresponding to the distance between the ultrasonic probe 50 and the desired location of the cryoprobe 80. Thus, the laser 60 will be moved until it is positioned in spaced opposing alignment with the tissue area of the patient to be treated.

The switch (designated 62 in FIG. 5) of the laser 60 is closed so that the laser is energized to emit a light beam 85 that is aimed towards the patient's skin, whereby to establish a target thereagainst through which a cryosurgical probe 80 and/or the positioning needle will be inserted to penetrate the body. Because the stereotactic surgical guide 1 of this invention is carried on the elongated shaft 58 of probe 50, the laser 60 is spaced from the target made by the light beam 85 against the patient's skin. Accordingly, the surgeon will have sufficient room available so as to be able to easily access the target area and insert the cryosurgical probe 80 and/or positioning needle into the prostate or other organ of the patient undergoing treatment. This advantage overcomes a significant problem inherent with conventional guides which are known to undesirably block or impede access to the point of entry for the cryoprobe.

With one or more of the cryosurgical probes 80 inserted as shown in FIG. 1, the laser 60 is deenergized and the laser beam 85 is extinguished. The stereotactic surgical guide 1 is then removed from the ultrasonic probe 50 so that the probe 50 can be used as usual to detect the angle and depth of the cryosurgical probes 80 based upon the visual image that is observed by the surgeon on the monitor of the ultrasound machine. In this regard, the well known Seldinger access technique may be employed to insert the cryosurgical probes 80 through the body so as to be capable of delivering a cryogen to the patient's prostate or other organ to form a series of strategically placed iceballs for the purpose of destroying cancerous cells in a localized tissue area. By way of example only, reference may be made to my copending patent application Ser. No. 08/934,497 filed Sep. 19, 1997 in which particular cryoprobe configurations are disclosed that are applicable to the invention described herein.

While the stereotactic surgical guide which forms this invention has been described as having specific application for accurately locating cryosurgical probes in the body of a patient undergoing cryosurgery, it is to be understood that the combination stereotactic surgical guide and ultrasonic probe have other applications as weft. For example, the aforementioned combination can also be used to accurately locate a hypodermic needle in a patent's vein, to enable a cannula to be placed so that a biopsy can be taken from a patient's tissue, to place an IV catheter to deliver a pharmaceutical or medication, and similar medical applications where ultrasonic imaging is used to enable a surgeon to penetrate the body at a particular location with respect to an organ or vessel.

I claim:

1. In combination:
    an ultrasonic probe to provide a visual image of a patient's body; and
    a surgical guide to be coupled to said ultrasonic probe to enable a needle probe to penetrate the body cavity of a patient at a particular location with respect to an organ or vessel of the patient undergoing treatment, said surgical guide comprising;
    a clamp by which to detachably connect said surgical guide to said ultrasonic probe;
    a plate for carrying a light source;
    a light source coupled to said plate; and
    position adjusting means interconnected with said plate to adjust the position of said plate and the light source coupled thereto,
said position adjusting means operated to correspondingly move said plate relative to said ultrasonic probe until said light source coupled to said plate lies in spaced opposing alignment with the patient's organ or vessel to be treated, said light source being energized to emit a light beam towards the patient's body to establish a target thereagainst to indicate the place for the needle probe to penetrate the body to reach the organ or vessel.

2. The combination recited in claim 1, wherein said ultrasonic probe has an elongated shaft and an ultrasound transducer located at one end of said shaft, said clamp detachably connecting said surgical guide to the shaft of said ultrasonic probe.

3. The combination recited in claim 2, further comprising an alignment needle and a needle passageway extending through said position adjusting means for removably receiving said alignment needle therein, the longitudinal axes of said alignment needle and said ultrasonic probe being arranged in parallel alignment with one another such that said alignment needle is spaced from said ultrasonic probe and located directly above the ultrasound transducer thereof.

4. The combination recited in claim 3, where the longitudinal axes of said alignment needle, said light source and said ultrasonic transducer are all arranged in spaced parallel alignment one above the other.

5. The combination recited in claim 2, wherein said clamp has a pair of gripping members that are pivotally connected together, the shaft of said ultrasonic probe received and retained between said pair of gripping members by which said surgical guide is coupled to said ultrasonic probe.

6. The combination recited in claim 1, wherein said position adjusting means includes a threaded worm drive interconnected with said plate such that a rotation of said threaded worm drive causes a corresponding movement of said plate and the light source coupled to said plate.

7. The combination recited in claim 6, wherein said position adjusting means also includes a plate support connected to said plate and coupled to said worm drive, said plate support riding along said worm drive in response to a rotation of said worm drive for causing the movement of said plate and said light source coupled thereto.

8. The combination recited in claim 7, wherein said position adjusting means also includes at least one guide rail running parallel to said worm drive, said plate support sliding against said guide rail and riding along said worm drive in response to a rotation of said worm drive for causing the movement of said plate and said light source coupled thereto.

9. The combination recited in claim 7, wherein said position adjusting means also includes a pair of guide rails running in spaced parallel alignment to each other and to said worm drive, and a fastener connected to said plate support and extending between said pair of guide rails to hold said plate support against said guide rails, said plate support sliding against said pair of guide rails and riding along said worm drive in response to a rotation of said worm drive for causing the movement of said plate and said fight source coupled thereto.

10. The combination recited in claim 1, wherein said fight source is a laser.

* * * * *